United States Patent [19]

Kesling

[11] Patent Number: 4,859,179
[45] Date of Patent: Aug. 22, 1989

[54] EDGEWISE BRACKET WITH SVED SHAPED SLOT AND CONTROL MEANS

[75] Inventor: Peter C. Kesling, LaPorte, Ind.

[73] Assignee: TP Orthodontics, Inc., Westville, Ind.

[21] Appl. No.: 935,586

[22] Filed: Nov. 26, 1986

[51] Int. Cl.$^4$ .............................................. A61C 3/00
[52] U.S. Cl. .......................................... 433/8; 433/16
[58] Field of Search ...................... 433/8, 9, 10, 11, 16

[56] References Cited

U.S. PATENT DOCUMENTS

| | | | |
|---|---|---|---|
| 3,772,787 | 11/1973 | Hanson | 433/11 |
| 3,879,850 | 4/1975 | Wallshein | 433/11 |
| 4,248,588 | 2/1981 | Hanson | 433/11 |
| 4,299,569 | 11/1981 | Frantz | 433/8 |
| 4,419,078 | 12/1983 | Pletcher | 433/11 |
| 4,575,337 | 3/1986 | Fujita | 433/8 |
| 4,614,497 | 9/1986 | Kurz | 433/8 |
| 4,664,626 | 5/1987 | Kesling | 433/8 |

Primary Examiner—John J. Wilson
Attorney, Agent, or Firm—Lloyd L. Zicker

[57] ABSTRACT

An edgewise bracket with a Sved shaped archwire slot and stop means for coating with the bracket and an archwire for limiting crown tipping or root uprighting movements so as to achieve predetermined uprighting or tip values. The archwire slot includes edges for permitting pivotal tipping or uprighting movement between the bracket and the archwire and surfaces inclined in excess of any desired tipping or uprighting movement. The stop means may be in the form of pins mounted on a base for the bracket, a clip snap fitting over the bracket and having stop tabs or lugs for engaging the archwire, or elastic ligatures having enlargements that engage the archwire and induce the bracket to remain in a predetermined position relative to the archwire.

12 Claims, 2 Drawing Sheets

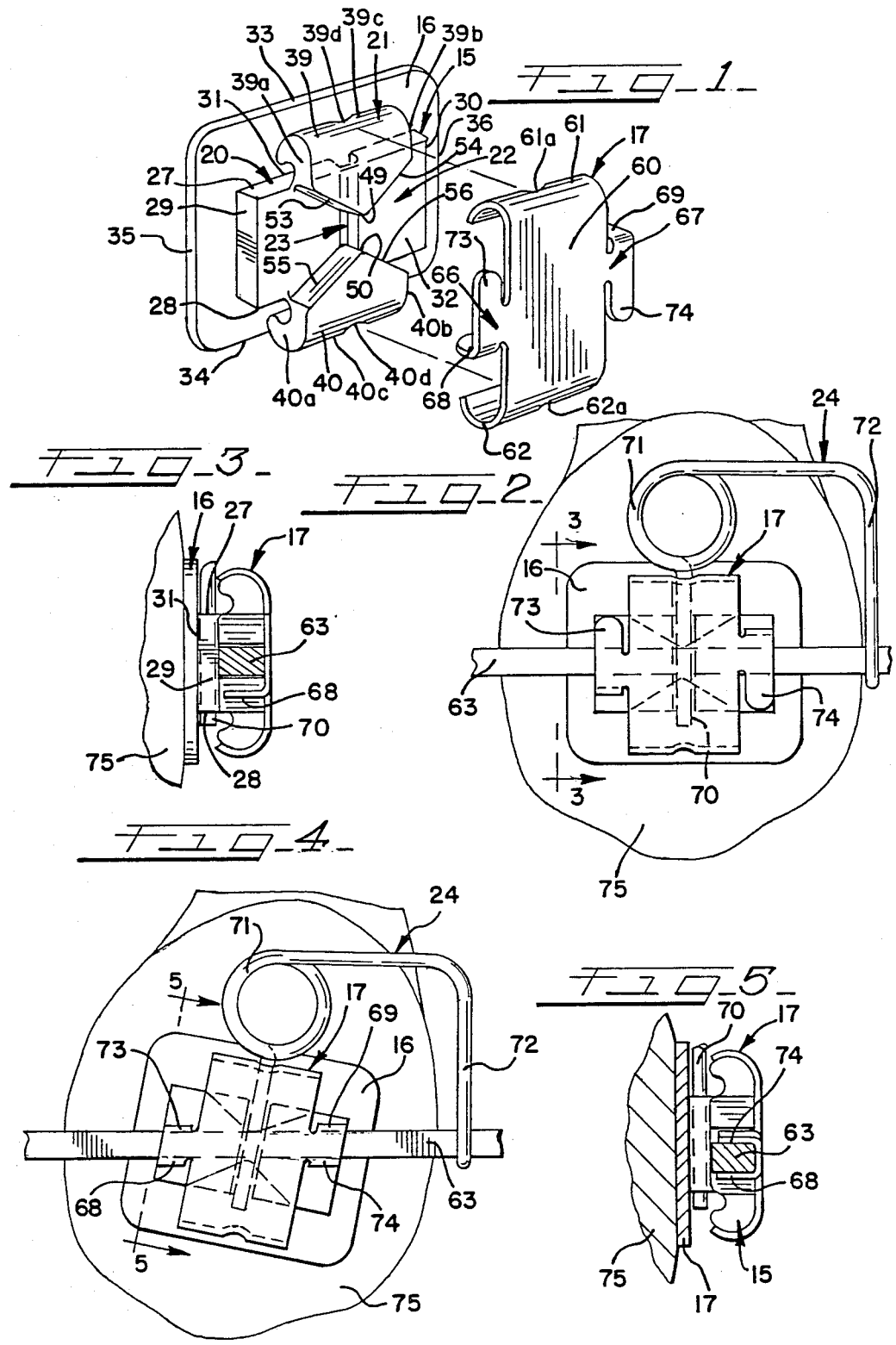

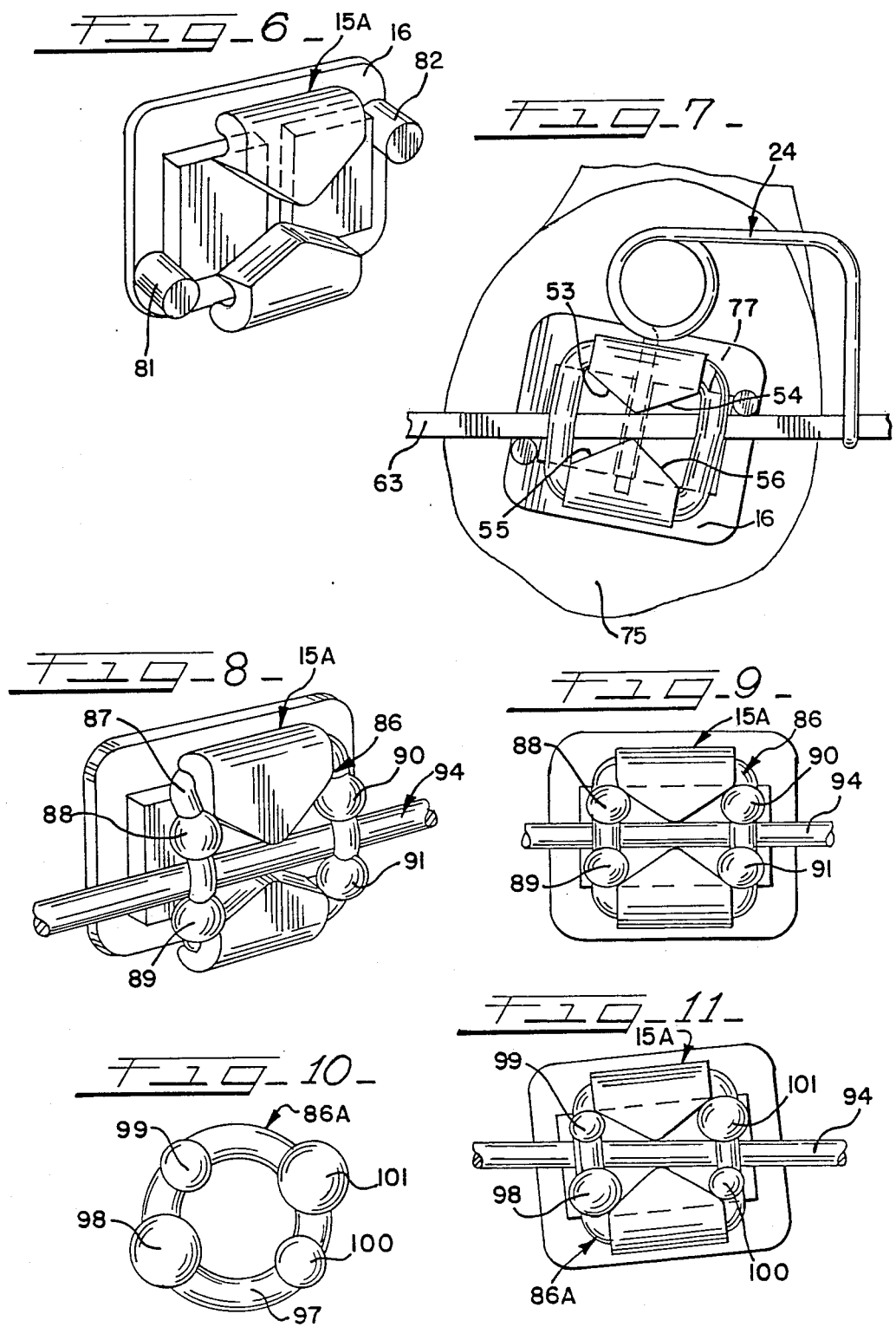

EDGEWISE BRACKET WITH SVED SHAPED SLOT AND CONTROL MEANS

This invention relates in general to an orthodontic bracket for producing tooth movement, and more particularly to an orthodontic bracket for producing mesial-distal tooth movement through crown tipping and root uprighting movments, and still more particularly to an edgewise bracket for moving teeth with intraoral generated forces, while permitting a range of free crown tipping and producing predetermined final degree values of root uprighting and/or torque.

The terms "tipping" and "uprighting" relate to movements of teeth caused by the application of selected forces. Generally, "tipping" refers to either labial-lingual or mesial-distal movement of the crown of a tooth, while "uprighting" refers to either mesial or distal movement of the tip (apex) of the root of a tooth. Tipping herein will be in the mesial-distal direction unless otherwise specified. Torque generally refers to the movement of the root of a tooth in the labial-lingual direction as a result of forces being applied to the crown of the tooth. Thus, crown movement will be referred to as tipping, while root movement will be referred to as uprighting or torqueing. The use of "and/or" herein is intended to cover three alternatives. For example, "mesial and/or distal archwire stops" means mesial and distal archwire stops or mesial archwire stops or distal archwire stops.

BACKGROUND OF THE INVENTION

There are a number of orthodontic techniques in use, the most common being the edgewise and the Begg techniques. Within the ambit of the edgewise technique, the most popular form is referred to as the straight-wire technique, although all forms of edgewise technique heretofore generally use edgewise brackets having horizontally extending archwire slots, the openings of which face horizontally. The bracket configuration for the Begg technique utilizes a vertically extending archwire slot which permits materially greater free tipping of teeth during treatment than most heretofore known edgewise brackets.

Heretofore, the only long ago edgewise bracket known allowing substantially unlimited tipping or uprighting movements was developed by Alexander Sved, where the archwire slot, hereafter called "Sved shaped", includes opposed pivot edges and surfaces widely diverging from the pivot edges. The Sved bracket is shown in the July, 1938 issue of the American Journal of Orthodontics, pages 635-654.

More recently, I conceived an edgewise bracket that permits tipping and eliminates the need for headgear, as disclosed in my copending application Ser. No. 879,072, filed June 26, 1986, now abandoned.

The need for moving teeth mesial-distally is usually caused by spaces created by small or missing teeth. It is customary in the Begg technique to close these spaces or move teeth by first tipping the clinical crowns toward the open area and then uprighting the roots to achieve the desired final uprighting or tip angles. For closing such open sites when using the edgewise technique, it is customary to bodily move the teeth. It is well known that the forces needed, discomfort, and time required for closing spaces by tipping and uprighting movements is much less than that required for bodily moving the teeth.

Where teeth are initially tipped and standard edgewise brackets are mounted on the teeth to provide treatment through the edgewise technique, it is difficult, if not impossible, to engage a relatively large diameter or stiff archwire into the respective archwire slots. The same problem exists if teeth with edgewise brackets become tipped during the course of treatment. And yet, such larger diameter, stiffer archwires are often necessary to control the vertical and horizontal positions of the teeth in the jaws. Therefore, the smaller and more flexible archwires which must be utilized can cause the anterior teeth to elongate and/or the posterior teeth to move laterally. The most common method of preventing these problems includes application of extraoral forces of the arches.

If resilient archwires are deflected to fully engage angulated slots where teeth are tipped, the occlusal plane or level of the biting edges of the teeth can be adversely affected by the forces applied through these archwires. Usually, the anterior teeth are elevated out of their sockets, resulting in an unhealthy deep anterior overbite condition. This is one of the reasons tipping of teeth in the edgewise technique is avoided. Moreover, the very design of the well known edgewise bracket prevents teeth from becoming tipped during treatment. It will be understood that the "occlusal plane" as used herein is a plane containing the contact points between the upper and lower teeth, and it generally lies ninety degrees to the vertical lines used for references when determining and describing the amount of tip or torque desired for each tooth.

In Begg brackets, sometimes referred to as ribbon arch or lightwire brackets, it is usually possible to engage larger stiffer archwires in the archwire slots because the opening of the slots face vertically, thereby permitting ease of archwire engagement in brackets mounted on tipped teeth.

It has been suggested that the edgewise slot be shortened mesio-distally or altered to define opposing one point contacts to increase the degree of tipping. However, the former still restricts tipping the loses its effectiveness to control/achieve the final degree of uprighting desired. The later (altered) bracket can permit free tipping but has no ability to control or create the final, desired degree of uprighting.

While Begg brackets that permit but limit tipping and/or uprighting are known, edgewise brackets with similar functions are not known except in my invention of the above copending application.

It has also been known to use combination brackets having both labially or horizontally facing horizontal archwire slots and gingivally facing vertical archwire slots where the vertical slots would be used during early stages of orthodontic treatment to allow the crowns of the teeth to tip toward their final positions. Then in the final stage an archwire can be deflectively received by the horizontal slots. However, while this will tend to upright the teeth, it will also tend to deepen the anterior bite condition and therefore headgear for producing extraoral forces may be required to counteract such adverse conditions. Headgear comprises using the patient's head or neck as a point of anchorage for delivering relatively heavy forces to the teeth.

Where combination brackets are used, it has also been suggested that two archwires be used, one in the horizontal slots and one in the vertical slots. A lighter more resilient archwire is deflected to seat in the angulated horizontal slots, while a heavier stiffer archwire is engaged without deflection into the vertical slots. The heavy wire helps stabilize the reciprocal forces delivered to the teeth from the lighter deflected archwire as it returns to its passive straight arch form. The use of two archwires is cumbersome, unaesthetic, and creates undesirable food traps.

In the edgewise procedure teeth are moved bodily in their upright positions toward one another to close spaces. Such movement requires up to twice as much force and/or time as when moving teeth by a combination of tipping and uprighting movements. Normally, crown tipping is followed by root uprighting. Moreover, the bodily movement method in the edgewise technique most often requires the application of extraoral force supplied by headgear. Clinical experience indicates that the use of such extraoral force has caused hundreds of soft tissue injuries including many cases of partial and even total blindness as a result of accidents occurring while wearing headgear.

SUMMARY OF THE INVENTION

The present invention obviates the above-mentioned difficulties in providing an improved edgewise bracket for use in the straight wire technique having a Sved shaped archwise slot for moving teeth to retract teeth and/or close spaces which provides controlled tipping or uprighting and essentially eliminates the need to apply extraoral force through headgear.

The present invention relates to an improved edgewise bracket. While particularly useful for moving teeth and closing spaces in a straight-wire technique, it can be used with any type of technique. The bracket of the invention resembles an edgewise bracket in that it includes a tie wing and a horizontally labially opening archwire slot. Stop means is provided to limit tipping and/or uprighting movements. The archwire slot is sized and formed to received either a heavy or a light archwire and Sved shaped to allow substantially unlimited tipping and uprighting movements. The archwire may be round or rectangular. Crown tipping and root uprighting movements may be accomplished by use of suitable elastics, springs and other auxiliaries intraorally.

The stop means coacts with the bracket and archwire to limit tipping and uprighting movement. The Sved archwire slot defines opposed labiolingually extending pivot edges and mesiodistally extending surfaces diverging from opposite sides of the pivot edges. The stop means may take the form of pins extending from bases on which the brackets are mounted, clips mountable over the bracket and having tabs, and elastomeric devices in the form of elastic ligatures.

For the purpose of accommodating the use of uprighting springs and other auxiliaries, a vertical slot is provided in the base of the bracket at the tooth-mounting side. Rotation control extensions extending mesially and distally from the archwire slot may also be provided.

It is therefore an object of the present invention to provide an edgewise bracket with a Sved shaped archwire slot and stop means for limiting tipping and uprighting movements.

Another object of the present invention is in the provision of an edgewise bracket with a Sved shaped archwire slot and stop means for use in edgewise and other techniques having uprighting limit means that avoid overmovements.

A further object of the present invention is in the provision of an edgewise bracket for use in moving teeth with a Sved shaped archwire slot and stop means which substantially eliminates the need to apply extraoral forces.

A further object of the present invention is in the provision of an edgewise bracket with a Sved shaped archwire slot and stop means for use in repositioning teeth anterior-posteriorly which substantially eliminates the need to use headgear.

Another object of the invention is to provide an edgewise bracket with a Sved shaped archwire slot and a stop means to control tipping or uprighting in the form of pins extending from a base on which the bracket is mounted.

Another object of the invention is to provide an edgewise bracket with a Sved shaped archwire slot and stop means for controlling tipping or uprighting in the form of a clip to be mounted over the bracket and which includes tabs for engagement with the archwire.

Another feature of the invention is to provide a stop means for a bracket having a Sved shaped archwire slot including an elastic ligature having enlargements for coacting with the archwire and bracket to stabilize bracket movement relative to the archwire in a predetermined position.

Other objects, features and advantages of the invention will be apparent from the following detailed disclosure, taken in conjunction with the accompanying sheets of drawings, wherein like reference numerals refer to like parts.

BRIEF DESCRIPTION OF THE DRAWINGS

FIG. 1 is a perspective exploded view of a bracket and clip combination where the clip serves to retain the archwire in the archwire slot and define stop means for limiting tipping or uprighting movment;

FIG. 2 is a front elevational view of the bracket and clip shown in FIG. 1 with the bracket mounted on a tooth and wherein the clip is assembled on the bracket and illustrating an uprighting spring mounted for purposes of applying an uprighting force to the tooth;

FIG. 3 is a side elevational view of the assembly illustrated in FIG. 2 and taken substantially along line 3—3 thereof;

FIG. 4 is a view similar to FIG. 2 but with the tooth in its final uprighted position and also illustrating use of bendable tabs coacting with prebent tabs on the clip to maintain a predetermined positional relationship between the bracket and the archwire;

FIG. 5 is a side elevational view taken along line 5—5 of FIG. 4;

FIG. 6 is a perspective view of the bracket of FIG. 1 but illustrating a modified stop means in the form of pins extending from the base to limit relative movement between the archwire and the bracket;

FIG. 7 is a front elevational view of the bracket of FIG. 6 with the archwire mounted in place and illustrating an uprighting spring causing the bracket to be moved to the predetermined position where the archwire abuts the stop pins;

FIG. 8 is a perspective view of a bracket like that in FIG. 1 with an archwire mounted in the slot and a modified stop means in the form of an elastic ligature having ball-shaped enlargements for coacting with the archwire and the bracket to centrally dispose the archwire relative to the bracket;

FIG. 9 is a front elevational view of the assembly shown in FIG. 8;

FIG. 10 is a front elevational view of a modified elastic ligature wherein two of the enlargements are larger than the other two to stop movement at an angular position between the archwire and bracket; and FIG. 11 is an assembly showing the elastic ligature of FIG. 10 in mounted position and the resulting stabilized angular position between the archwire and the bracket after movement has been completed.

DESCRIPTION OF THE INVENTION

The improved bracket of the invention may be generally referred to as an edgewise bracket since it includes a ligature tie wing and a horizontally opening archwire slot in its outer face. While the bracket of the invention may be used in any one of many edgewise techniques, it may also be used in other techniques. Normally, it will be used in a system having edgewise-type brackets, and will be described as being used in the straight wire technique where a heavy straight archwire is used as a reference during much of the treatment.

The bracket of the invention functions primarily to move teeth mesial-distally along an archwire by a combination of tipping and uprighting actions. Either round or rectangular archwire may be used during this tooth-moving process.

Teeth that require orthodontic treatment are quite often tipped mesial-distally at the beginning of or during the course of movement. The configuration of the horizontal archwire slot in the bracket of this invention permits the initial engagement of an archwire in the brackets on such tipped teeth with little or no deflection. Deflecting the archwire could require greater force to be applied and/or result in loss of control in the vertical dimension, i.e., the undesired depression and/or elongation of teeth. This archwire slot in the bracket of the present invention permits the teeth to tip mesial-distally during treatment without deflecting the archwire.

Inasmuch as both elastic traction devices and/or springs may be used during the tooth-moving process, and either or both of which may apply forces of a magnitude that could overpower a highly resilient archwire such as of the nickel titanium or metal core-plastic type, it is advantageous to use a relatively stiff or rigid archwire to define a reference. With the bracket of the present invention, it will be appreciated that the archwire can be disposed in substantially parallel relation to the occlusal plane even when engaged in brackets on mesial-distally tipped teeth. Thus, the archwire can be of a size and stiffness compatible with the reciprocal movement forces to be encountered so that the tipping and uprighting movements produced will give the desired results.

The bracket of the invention can be made of a suitable metal, such as stainless steel, and it may be machined, sintered or cast in any known manner. The bracket may be made and then suitably secured to a base that would be bondable to a tooth, or the bracket and base may be cast together as a single unit. While it is preferred that the bracket be made of metal, it will be appreciated that it could be made of ceramic or plastic or plastic with a metal lined archwire slot. It is important that the bracket have sufficient strength to withstand the forces employed during the tooth-moving process so as to avoid failure and interruption of treatment. It may also be appreciated that the bracket may otherwise be attached to a tooth by the usual banding methods. In all cases the bracket will be mounted to the crown of the tooth, and aligned with the long axis of the crown so that the tooth will attain the position finally desired.

For purposes of describing the invention and for purposes of clarity, the drawing illustrations principally relate to showing the straight-wire technique wherein the archwire will be disposed in substantially parallel relation to the occlusal plane, and the form of the stop means limiting movement in each bracket may be different to achieve varying degrees of final mesiodistal root uprighting according to the desires of the orthodontist and the needs of each patient. While the illustrations relate to uprighting, it will be appreciated that tipping can also be controlled by appropriately positioning the stop means.

Referring now to the drawings, and particularly to the embodiment of FIGS. 1 to 5, the bracket for which the stop means in one of its various forms is provided is generally indicated by the numeral 15 and is shown in mounted relation on a mounting pad or base 16. As seen in FIG. 1, the stop means for controlling tipping movement between the bracket and the archwire is in the form of a clip 17 snap-fittable over the face of the bracket.

While the bracket 15 is shown mounted on a base or pad that would be in turn mounted by direct bonding onto the crown of a tooth, it will be appreciated that the bracket could be suitably mounted onto a band that would be cemented to a tooth. For simplicity purposes, the bracket is illustrated in all of the drawings as being mounted on a pad or base.

The bracket 15 includes a base portion 20 and a tie wing 21 having a Sved shaped archwire slot 22. A vertically extending slot 23 is provided in the base for anchoring auxiliaries such as the uprighting spring 24 shown in FIG. 2. It may also anchor rotating springs.

The base 20 includes upper and lower parallel horizontally extending outer walls 27 and 28 and opposed vertically extending outer walls 29 and 30 defining a rectangular base. The base portion further includes a back side 31 suitably attached to the pad or base 16 and a front archwire bearing surface 32. It will be appreciated that the upper and lower walls 27 and 28 and the opposed side walls 29 and 30 are disposed parallel to upper and lower pad edges 33 and 34 and opposed side edges 35 and 36, respectively. While this parallel relationship can assist in orienting the bracket during mounting, it is not critical to the invention. The vertical slot 23 parallels the opposed side walls 29 and 30 of the base portion and is disposed along the vertical axis.

The tie wing 21 includes upper and lower tie wing tipes 39 and 40 having respectively vertically extending opposed vertical walls 39a, 39b, 40a, 40b, which extend parallel to the base portion opposed side walls 29 and 30. Walls 39a and 40a are coplanar as are walls 39b and 40b. The tips further include mesiodistally extending edges 39c and 40c which are parallel to each other and also parallel to the upper and lower horizontally extending walls 27 and 28 of the base portion. Again, this parallel relationship is not necessary to the invention, but may assist in orientation during bracket mounting. The cross sections of the tie wings are in the usual form of hooks for facilitating the retention of ligatures and the upper and lower edges are arcuately formed in the usual manner and which facilitates the use of the snap-on clip 17.

The archwire slot 22 horizontally opens toward the labiobuccal and being Sved shaped includes labiolingual edges 49 and 50 against which the archwire will pivot. Diverging from the pivot edges are upper inclined surfaces 53 and 54 and lower inclined surfaces 55 and 56, thereby defining V-shaped surfaces. As seen in FIG. 2, the inclinations are equal and opposite. They further are such that they incline from the horizontal beyond any desired tipped or uprighted position. Thus, they do not function to limit tipping or uprighting movements during any normal course of treatment. The width of the base portion 20 is such that it extends the face of the archwire slot both mesially and distally of the slot in order to provide a bearing surface for the archwire mesially and distally of the slot and thereby increase rotational control about the long axis of the tooth. It will be appreciated that the bracket may or may not have these extensions but that with the extensions better rotational control is obtained. While the bracket illustrated defines a rectangular mesial-distal profile, it may be formed to define other profiles.

With respect to the embodiment of FIGS. 1 to 5, the stop means for controlling or limiting upright movement is in the form of a clip 17 and which includes a one-piece body having a planar 60 with upper and lower curved ends 61 and 62 that mate with the upper and lower curved surfaces of the tie wing tips when the clip is mounted on the bracket. The clip may be made of a suitable metal or plastic. The planar panel 60, as well as the tips, is generally formed to completely cover the mesiodistal or labial face of the bracket the wing and the tips, although it could be sized to cover only a portion. Once the clip is mounted onto the tie wing, it will be appreciated that it closes the slot and functions to retain an archwire placed therein in association with the bracket such as shown by the archwire 63.

Extending from opposite side edges of the planar panel 60 are archwire engaging members 66 and 67 which include prebent stop tabs 68 and 69 that extend into the area of archwire movement, as seen in FIG. 3.

For limiting relative movement between the archwire and the bracket, the position of the stop lugs 68 and 69 will depend upon the specific tooth for which the bracket is designed as well as the movement function desired by the orthodontist. While it would not normally be the preference of the orthodontist to limit tipping movement, it is important to obtain the finally desired uprighting inclination as would be possible with the clip, as illustrated in FIGS. 1 to 5. It is always a desire to orient the crown and position it in the ideal location, which location normally constitutes some degree of tip value. When utilizing the bracket and clip combination to close a space, the crown is first tipped toward the open site, and when disposed in that site the root is uprighted to a position where the long axis of the crown reaches a desired tip angulation. The amount of initial crown tipping will depend upon the amount of retraction or protraction desired for a tooth.

For a specific tooth, the angle of inclinatin or position for the root uprighting stops, such as 68 and 69 for the clip 17, would tend to be the same for all patients depending upon the orthodontist's treatment goals. Bending the tabs relative to the main body of the clip could modify the stop position and final angle of inclination. When retracting or protracting a tooth, forces will be induced to tip the tooth mesially or distally. The crown is then held horizontally to prevent horizontal or lateral movement along the archwire, while the root is then uprighted over the crown to the ideal or desired final inclination. These so-called ideal final inclinations may differ among orthodontists as does beauty in the eyes of the beholder. Where the term "angle of inclination" is used herein, it is intended to cover positioning of a tooth vertically or at an inclined position to the vertical. Commonly used ideal or desired angles of inclination for each particular tooth have been proposed. The angle of inclination is measured to the distal between the vertical axis of the mouth and the long axis of the clinical crown of a tooth. For example, the common ideal angles of inclination for the upper teeth accepted by many, left and right, are:

5 degrees for a central,
9 degrees for a lateral,
11 degrees for a cuspid,
2 degrees for a bicuspid, and
5 degrees for a molar.

The common inclination angles for lower teeth, left and right, are:

2 degrees for centrals and laterals,
5 degrees for the cuspids, and
2 degrees for the bicuspids and molars.

Referring again to the embodiment of FIGS. 1 to 5, the uprighting spring 24 for producing a force to upright the tooth relative to the wire includes a tail 70 received in the vertical slot 23, one or more force-producing coils 71, and an activating arm 72 having a hook for engaging the wire. The spring induces a force to drive the bracket and tooth in a clockwise direction, as viewed in FIG. 2, until the tooth reaches the angle of inclination, as shown in FIG. 4, wherein further movement is stopped by the prebent stop tabs 68 and 69.

When that angle of inclination is reached and it is desired to hold the tooth in that position, bendable holding tabs 73 and 74 forming a part of the archwire engaging members of the clip may be bent over and against the archwire along with the tabs 68 and 69, as seen in FIGS. 4 and 5, to maintain the angle of inclination during continued treatment of the patient. The operation of the clip and bracket may be further appreciated by viewing sequentially FIGS. 2 and 4 where the bracket is mounted on tooth 75.

It will further be appreciated that the tipping or uprighting spring can be removed once the tabs 73 and 74 have been bent into position against the wire, as it is no longer needed. The clip is generally somewhat resilient and therefore will spring when mounted over the face of the bracket and snap into place. In order to prevent lateral sliding on the bracket, indents 39d and 40d are provided on the tie wings tips to coact with detents 61a and 62a formed on the upper and lower curved ends of the clip.

It can therefore be appreciated that the tabbed clip 17 forms one version of a stop means that controls and limits movement between the archwire and the bracket having a Sved shaped archwire slot.

A modified stop means according to the invention is illustrated in FIGS. 6 and 7, wherein the archwire is held in place on the archwire slot in the conventional manner by a standard elastic ligature 77. Stop means for limiting uprighting movement includes pins 81 and 82 mounted on the base 16 and extending labiobuccally and into the path of movement of the archwire. These pins are disposed to limit movment, as illustrated in FIG. 7, such that the proper angle of inclination of the crown of the tooth is obtained as desired. The pins prevent relative movement between the archwire and the bracket short of the inclined surfaces 54 and 55 of the tie wing tips. It will be appreciated that this embodiment functions to limit uprighting movement in an equivalent manner to the embodiment of FIGS. 1 to 5.

It is well known that an elastic ligature produces a "hammock effect" that tends to center the archwire in the bracket slot or, since the wire serves as a reference, tends to center the bracket slot relative to the wire. However, this force will not provide positive control or movement, and it is necessary to exert a force that will produce positive movement. Devices for producing positive movement to urge the stops or other surfaces associated with the archwire slot to the archwire include springs and elastics.

Another form of stop means for limiting the tipping movement between the bracket and the archwire is illustrated in FIGS. 8 and 9, wherein the stop means comprises a unique elastic ligature 86 having an elastic strand 87 with integrally formed enlargements 88, 89, 90 and 91. The enlargements 88 to 91 are ball-shaped of equal size and arranged in pairs with 88 and 89 constituting one pair and 90 and 91 constituting the other pair. The enlargements of each pair are equally spaced apart between them and equally spaced apart on the strand so as to produce the desired movement forces between the bracket and the archwire. While the enlargements are ball-shaped, they could be otherwise shaped, and they are illustrated in this embodiment to be of such a size as to fit between the archwire and the mesial and distal sides of the bracket.

The bracket 15A is identical to that shown in FIGS. 6 and 7, and when the elastic ligature 86 is hooked over the upper and lower tie wing tips so that the enlargement pairs are disposed at the mesial and distal sides of the bracket and in stradding relation with the archwire, it will tend to center the bracket on the archwire as shown. As seen in both FIGS. 8 and 9, the archwire, here designated by the numeral 94, is round, although it will be appreciated that rectangular archwire may be used with this elastic ligature. Similarly, a round archwire could be used with the above embodiments.

So, with the elastic ligature in place as illustrated, it will tend to urge the positional relationship between the bracket and the archwire such that the archwire will be parallel to the mesiodistal axis of the bracket, as seen in FIG. 9. This position will also be perpendicular to the vertical axis of the bracket and the long axis of the clinical crown. Thus, the elastic ligature 86 will produce a force to centrally position the bracket relative to the archwire. As above noted, a standard ligature produces the centering "hammock effect", but this modified ligature with ball-shaped enlargements will more positively produce the centering effect by firmly engaging the archwire. More particularly, other elastics or springs would normally be used to produce a movement force between the archwire and the bracket, and the enlargements on ligature 86 will serve as a stop means once the bracket has been moved relative to the archwire to the center position shown.

Where it may be desired to use an elastic ligature as a stop means and to obtain an angular relation between the bracket and the archwire, as illustrated in FIG. 11, the elastic ligature may take the form shown in FIGS. 10 and 11 and generally designated by the numeral 86A. In this form two pair of enlargements are provided on an elastic strand 97 where each pair includes ball-shaped enlargements 98, 99, 100 and 101. Enlargements 98 and 101 are larger than the enlargements 99 and 100, so that when applied to a bracket to not only retain the archwire in place in the archwire slot, they also stabilize the relationship between the bracket and the archwire at an angular setting once it is reached, as seen in FIG. 11. It will be appreciated that the sizes of the enlargements can be controlled to provide the desired angular relation between the bracket and the archwire.

The enlargements are illustrated as being sized to fit between the archwire and the inclined surfaces of the bracket slot. They could be sized as in the embodiment of FIGS. 8 and 9 to fit between the archwire and the mesial and distal sides of the bracket. Similarly, the enlargements in FIGS. 8 and 9 could be sized to fit between the archwire and the inclined surfaces of the slot.

The elastic ligatures of FIGS. 8 to 11 may be made of any suitable elastomeric material that will provide the desired stop means function and the ultimate desired end result. These ligatues may be molded or otherwise formed.

While the stop means in each of the illustrated embodiments includes a stop at each side of the bracket pivot, it will be appreciated that a stop on one side coacting with one of the pivot edges will function to stop movement between the archwire and the bracket.

Thus, the present invention provides an edgewise bracket allowing controlled tipping and uprighting movements for effecting movement of teeth along the archwire without resorting to headgear and moving teeth bodily as is customary in the straight wire technique. By limiting tipping and/or uprighting, overmovements are avoided.

It will be understood that modifications and variations may be effected without departing from the scope of the novel concepts of the present invention, but it is understood that this application is to be limited only by the scope of the appended claims.

The invention is hereby claimed as follows:

1. An edgewise bracket adapted to be mounted on the crown of a tooth such that the vertical axis of the bracket substantially aligns with the long axis of the crown, said bracket having a body with a horizontally opening close-fitting archwire slot for receiving an archwire and a single tie wing having gingival and occlusal tips, said slot having a Sved shape such that it defines directly opposed wire pivot edges, said edges being spaced apart a distance substantially equal to the occlusogingival dimension of the archwire to be received by the slot, opposed mesiodistally extending surfaces diverging from opposite sides of said pivot edges a substantially equal amount, said surfaces being inclined from the horizontal beyond any desired tipped or uprighted positioned, whereby said bracket has a mesiodistal pivotal relation with said archwire, and stop means coacting with said bracket and said archwire in said slot for limiting the tipping or uprighting movement range to a desired value short of said inclined surfaces, said stop means including a base on which the bracket is mounted and at least one archwire stop pin extending from said base for limiting the tipping and/or uprighting movement of said bracket.

2. An edgewise bracket adapted to be mounted on the crown of a tooth such that the vertical axis of the bracket substantially aligns with the long axis of the crown, said bracket having a body with a horizontally opening close-fitting archwire slot for receiving an archwire and a single tie wing having gingival and occlusal tips, said slot having a Sved shape such that it defines directly opposed wire pivot edges, said edges being spaced apart a distance substantially equal to the occlusogingival dimension of the archwire to be received by the slot, opposed mesiodistally extending surfaces diverging from opposite sides of said pivot edges a substantially equal amount, said surfaces being inclined from the horizontal beyond any desired tipped or uprighted position, whereby said bracket has a mesiodistal pivot relation with said archwire, and stop means coacting with said bracket and said archwire in said slot for limiting the tipping or uprighting movement range to a desired value short of said inclined surfaces, said stop means including an elastic ligature in the form of an endless member hooked over said tips retaining the archwire in said slot and having enlargements along said member coacting with the archwire and said slot to resiliently hold said bracket in a predetermined position relative to the archwire.

3. The combination of claim 2, wherein said enlargements are ball shaped and of equal size and equally spaced apart to move the bracket to a position where the archwire is centrally located between the diverging surfaces.

4. The combination of claim 2, wherein said enlargements are ball shaped and sized to move said brackets to a position where the archwire is closer to certain of the diverging surfaces.

5. The combination of claim 2, wherein certain of the enlargements are larger than others.

6. An edgewise bracket adapted to be mounted on the crown of a tooth such that the vertical axis of the bracket substantially aligns with the long axis of the crown, said bracket including a base portion and a single tie wing extending therefrom having upper and lower tie wing tips between which is a mesiodistally extending close-fitting archwire slot for receiving an archwire, said tie wing defining a substantially rectangular mesiodistal profile, said slot being horizontally opening and having a Sved shape such that it defines directly opposed labiolingually extending pivot edges centrally disposed along a vertical center line, said pivot edges being spaced apart a distance substantially equal to the occlusogingival dimension of the archwire to be received by the slot, and opposed mesiodistally extending surfaces diverging from said pivot edges, said surfaces being inclined from the horizontal beyond any desired tipped or uprighted position, whereby said bracket has a mesiodistal pivotal relation with said archwire, and mesial and/or distal archwire stop means extending integrally from said bracket and laterally of the pivot edges for limiting tipping or uprighting movement to a desired value less than that of the inclined surfaces.

7. The combination of claim 6, which further includes a base on which the bracket is mounted, and said stop means including archwire stop pins extending from said base at opposite sides of the bracket to limit relative tipping or uprighting movement between the archwire and the horizontal axis of the bracket to an inclination value of less than the inclination of said archwire slot surfaces.

8. An edgewise bracket adapted to be mounted on the crown of a tooth such that the vertical axis of the bracket substantially aligns with the long axis of the crown, said bracket including a base portion and a single tie wing extending therefrom having upper and lower tie wing tips between which is a mesiodistally extending close-fitting archwire slot for receiving an archwire, said tie wing defining a substantially rectangular mesiodistal profile, said slot having a Sved shape such that it defines directly opposed labiolingually extending pivot edges centrally disposed along a vertical center line, said pivot edges being spaced apart a distance substantially equal to the occlusogingival dimension of the archwire to be received by the slot, and opposed mesiodistally extending surfaces diverging from said pivot edges, said surfaces being inclined from the horizontal beyond any desired tipped or uprighted position, whereby said bracket has a mesiodistal pivotal relation with said archwire, mesial and/or distal archwire stop means integrally with the bracket and laterally of the pivot edges for limiting tipping or uprighting movement to a desired value less than that of the inclined surfaces, and said stop means including an elastic ligature in the form of an endless member hooked over said tips retaining the archwire in said slot and having enlargements along said member coacting with the archwire and the slot to resiliently hold said bracket in a predetermined position relative to the archwire.

9. The combination of claim 8, wherein said enlargements are ball shaped and of equal size and equally spaced apart to move the bracket to a position where the archwire is centrally located between the diverging surfaces.

10. The combination of claim 8, wherein said enlargements are shaped and sized to move said bracket to a position where the archwire is closer to certain of the diverging surfaces.

11. The combination of claim 10, wherein certain of the enlargements are larger than others.

12. An edgewise bracket adapted to be mounted on the crown of a tooth such that the vertical axis of the bracket substantially aligns with the long axis of the crown, said bracket having a body with a horizontally opening close-fitting archwire slot for receiving an archwire, said slot having a Sved shaped such that it defines directly opposed wire pivot edges, said edges being spaced apart a distance substantially equal to the occlusogingival dimension of the archwire to be received by the slot, opposed mesiodistally extending surfaces diverging from opposite sides of said pivot edges a substantially equal amount, said surfaces being inclined from the horizontal beyond any desired tipped or uprighted position, whereby said bracket has a mesiodistal pivotal relation with said archwire, and stop means extending integral from said bracket for limiting the tipping or uprighting movement range to a desired value short of said inclined surfaces.

* * * * *

UNITED STATES PATENT AND TRADEMARK OFFICE
CERTIFICATE OF CORRECTION

PATENT NO. : 4,859,179
DATED : August 22, 1989
INVENTOR(S) : Peter C. Kesling

It is certified that error appears in the above-identified patent and that said Letters Patent is hereby corrected as shown below:

```
Col.  2, line 15, change "of" to --to--;
         line 43, change "later" to --latter--;
Col.  3, line 35, change "horizontally" to --horizontal--;
         line 38, change "received" to --receive--;
Col.  7, line 23, after "planar" insert --panel--;
         line 29, after "bracket" change "the" to --tie--;
Col.  9, line 33, change "stradding" to --straddling--;
Col. 11, line 24, change "brackets" to --bracket--;
Col. 12, line 47, change "shaped" to --shape--; and
```

Add the following references on the Title Page:

```
3,530,583    9/1970   P. E. Klein et al. . . . 433/11
3,641,672    2/1972   P. C. Kesling      . . . . 433/21
3,729,826    5/1973   P. C. Kesling      . . . . 433/13
4,551,094   11/1985   P. C. Kesling      . . . . 433/8
```

PUBLICATIONS

"Principles and Technique of Modified Edgewise Arch Mechanism", Alexander Sved, American Journal of Orthodontics and Oral Surgery, Vol. 24, No. 7, July, 1938, pp. 635-654.

UNITED STATES PATENT AND TRADEMARK OFFICE
CERTIFICATE OF CORRECTION

PATENT NO. : 4,859,179

DATED : August 22, 1989

INVENTOR(S) : Peter C. Kesling

It is certified that error appears in the above-identified patent and that said Letters Patent is hereby corrected as shown below:

Add the following references on the Title Page:

PUBLICATIONS

"256-LTD Begg Light Wire Bracket", Straight-Talk, TP
   Orthodontics, Inc., 1986

Signed and Sealed this

Tenth Day of July, 1990

Attest:

HARRY F. MANBECK, JR.

Attesting Officer    Commissioner of Patents and Trademarks